United States Patent [19]

Decker et al.

[11] 4,185,497
[45] Jan. 29, 1980

[54] ADIABATIC LASER CALORIMETER

[75] Inventors: Donald L. Decker; Paul A. Temple, both of Ridgecrest, Calif.

[73] Assignee: The United States of America as represented by the Secretary of the Navy, Washington, D.C.

[21] Appl. No.: 947,379

[22] Filed: Oct. 2, 1978

[51] Int. Cl.² .................................. G01K 17/00
[52] U.S. Cl. ...................................... 73/190 EW
[58] Field of Search ............... 73/190 H, 190 EW; 250/352; 356/432

[56] References Cited

U.S. PATENT DOCUMENTS

| | | | |
|---|---|---|---|
| 3,280,626 | 10/1966 | Stempel | 73/190 |
| 3,394,258 | 7/1968 | Schleiger et al. | 73/190 |
| 3,575,048 | 4/1971 | DeBenedictis | 73/190 |
| 3,622,245 | 11/1971 | Rasmussen | 73/190 X |
| 3,937,079 | 2/1976 | Chodzko | 73/190 |
| 3,999,706 | 2/1976 | Pinson | 73/190 |
| 4,019,381 | 4/1977 | Elmer | 73/190 |
| 4,088,447 | 5/1978 | Walker | 73/190 |

OTHER PUBLICATIONS

Cohen et al. "Loss Measurements in Optical Fibers", Z. Balometric Measuring & Instrumentation in Applied Optics vol. 13 #11 Nov. 1974 pp. 2523-2524.
Witte "Determination of Low Bulk Absorption Coefficients" in Applied Optics vol. 11 #4 pp. 777-779.
Ponnow et al. "Development of a Calorimetric Method for Making Precision Optical Absorption Measurements" in Applied Optics vol. 12 #5, 5/73, pp. 985-991.
Gray et al. A Dictionary of Physics 2nd Ed. 1975 p. 491.

Primary Examiner—Herbert Goldstein
Attorney, Agent, or Firm—R. S. Sciascia; W. Thom Skeer

[57] ABSTRACT

A device for measuring energy absorptance of a sample material. A temperature controlled enclosure, in which a sample is suspended, is placed in an evacuated container. Calibration is accomplished by means of a known power dissipation in the sample. The sample material is irradiated by an energy beam of known power and a temperature rise is compared to the calibration temperature rise. Means for scanning the sample is also provided.

10 Claims, 4 Drawing Figures

ADIABATIC LASER CALORIMETER

BACKGROUND OF THE INVENTION

1. Field of the Invention

This invention pertains to the field of measuring and testing apparatus. More particularly, this invention pertains to the field of calorimeters. In still greater particularity, this device pertains to an adiabatic calorimeter to measure the electromagnetic wave energy absorptance of a sample material.

2. Description of Prior Art

In general, calorimeters are used to make thermal measurements. Different types of calorimeters are used to make specific types of measurements. A discussion of different types of calorimeters can be found in *A New Dictionary of Physics* by Gray and Isaacs, second edition, 1975, Longman Group Limited, London.

For low temperature thermal measurements an adiabatic vacuum calorimeter was developed by Simon and Lange. A discussion of this calorimeter may be found on page 491 of *A New Dictionary of Physics*. In this device the calorimeter is suspended inside an enclosure. The calorimeter and the enclosure are placed in an evacuated container which is itself immersed in liquid hydrogen contained in a closed dewar vessel. The temperature of the liquid hydrogen may be varied by varying the pressure in the dewar vessel. For a determination of the specific heat of liquid hydrogen, the liquid hydrogen in the dewar vessel is boiled under reduced pressure until the hydrogen in the calorimeter is liquified. The enclosure is then evacuated and a current passed through a heater in the calorimeter. The liquid hydrogen vaporizes and is collected in a reservoir; and the mass of liquid vaporized being is deduced from the pressure and volume of the reservoir and the equation of state for hydrogen.

Calorimeters have also been used to measure laser energy. One such device is illustrated in U.S. Pat. No. 3,622,245 issued to Alvin L. Rasmussen on Nov. 23, 1971. In that device a mirror with a known specific heat capacity and known dimensions is irradiated with a laser beam until thermal equilibrium is achieved. The laser beam is reflected to a second mirror and then out of the apparatus. Temperature sensors are connected to each mirror and measure the energy absorbed by each mirror. The device also has an optional heater which may be positioned in the mirror as a calibration device. This type of calorimeter is a steady state calorimeter, that is, the energy beam heats the material until a steady state (constant elevated temperature) is reached. As such, quantities such as heat capacity and heat diffusivity of the irradiated material must be known. Because the calorimeter is not adiabatic, there are temperature variations in the sample such that the same area must be irradiated for each measurement in order to get consistent results. In addition, the sensitivity of steady state type calorimeters is less than adiabatic calorimeters such that low power sources cannot be used and small absorption measurements cannot be made.

Another steady state calorimeter is shown in U.S. Pat. No. 4,019,381 issued to Frank J. Elmer on Jan. 12, 1976. That device uses optical elements of uniform thickness supported by a mounting structure. The mounting structure has a small hole to allow electromagnetic energy to enter. Thermocouples are attached to the optical element and to the mounting structure. The energy absorbed by the optical element produces a temperature rise which is proportional to the power remaining in the beam after it passes through the optical element. This device has the same limitations as that previously described in that it is rate dependent, does not allow for scanning, and does not provide for low level optical measurement.

While the above-described devices are satisfactory for their intended purposes, a device having the capability to measure low level energy absorptance and, therefore, possessing greater accuracy, would be desirable. It would also be desirable to have sample scanning capability and to have a means for calibration in order that quantities such as the sample dimensions, heat capacity, and heat diffusivity need not be known.

SUMMARY OF THE INVENTION

The invention is directed to a method and apparatus for measuring the energy absorption of a sample material. The sample is suspended in a temperature-controlled enclosure by a clamp ring itself supported by very fine wires. The enclosure is then placed in an evacuated container. The enclosure is controlled so that its temperature is always that of the sample. Absolute electrical calibration is obtained by dissipating a known quantity of heat in a resistor attached to the clamp ring. A laser beam of known power and duration is used to irradiate the sample. The temperature rise of the sample and the power of the transmitted beam are then measured. The device is configured so as to allow scanning of the sample.

DESCRIPTION OF THE PREFERRED EMBODIMENT

Figure 1:
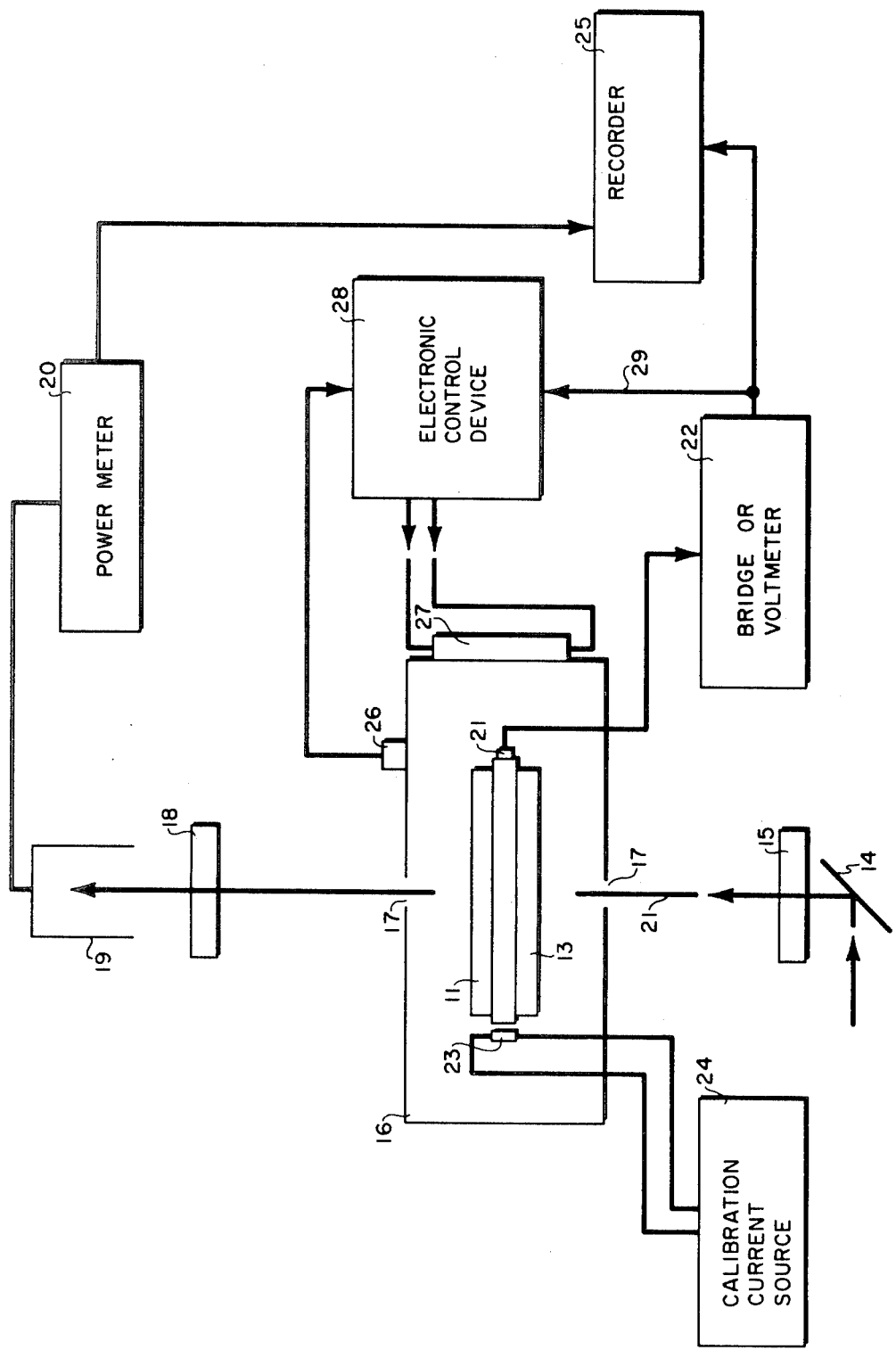
FIG. 1 is a block diagram of the invention.

Referring to FIG. 1, a sample material 11 is supported in the path of an energy beam 12 by a clamp ring 13. Energy beam 12, which may be an electromagnetic energy beam such as from a laser, is reflected from a mirror 14 and allowed to enter an evacuated container through an input window 15. Input window 15 may be a shutter or a lens. Energy beam 12 enters and exits a temperature-controlled enclosure 16 through small holes 17. The portion of energy beam 12 which is transmitted through sample 11 exits the evacuated container through exit window 18 and is detected by a power detector 19. A power meter 20 quantifies the power detected by detector 19.

A temperature sensing means 21, which may be a thermistor, thermocouple, semiconductor junction device, or other suitable sensor is mounted on clamp ring 13. Temperature sensing means 21 is connected to a bridge and voltmeter 22 or only a voltmeter if a thermocouple is used. A calibration means, which includes a heater 23, is also connected to clamp ring 13. Heater 23 may be a precision resistor or other suitable heater. A calibration current source 24 is connected to heater 23. A readout means 25, which may be a strip chart recorder, receives the outputs from power meter 20 and bridge and voltmeter 22.

The enclosure temperature controller means includes an enclosure temperature sensor 26, an enclosure heater 27, and an electronic control device 28. An electrical connector 29 allows the output from bridge and voltmeter 22 to be received by electronic control device 28.

Figure 2:
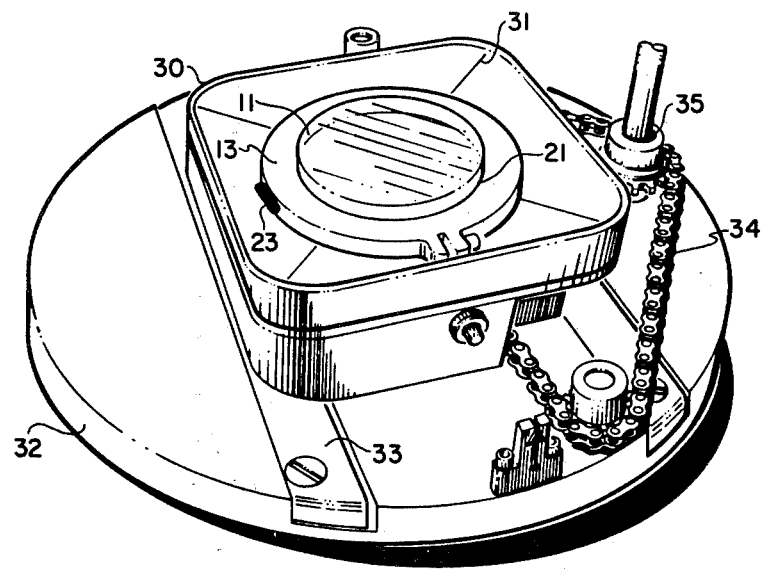
FIG. 2 is a view of the temperature controlled enclosure with the top removed.

Referring to FIG. 2, sample 11 is retained by clamp ring 13. Clamp ring 13 is suspended in a temperature-controlled enclosure base 30 by wires 31. Enclosure base 30 is slidably mounted on a vacuum container base 32. A pair of guide tracks 33 are made of a low friction material such as that sold under the trademark "teflon". Tracks 33 allow base 30 to be moved with respect to the energy beam such that sample 11 may be scanned. A roller chain 34 is attached to base 30 and is manually controlled by an adjusting rod 35. Temperature sensing means 21 and heater 23 are shown attached to clamp ring 13.

Figure 3:
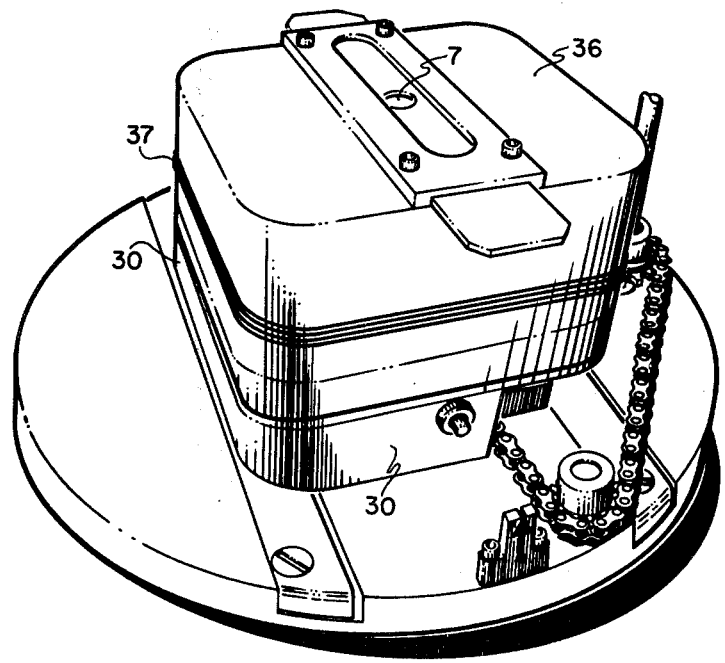
FIG. 3 is a view of the temperature-controlled enclosure with the top in place.

Referring to FIG. 3, base 30 is shown with temperature-controlled enclosure cover 36 in place. Output hole 17 is shown on cover 36. Heating elements 37 are shown mounted on cover 36. Base 30 and cover 36 comprise the temperature-controlled enclosure 16, shown in FIG. 1.

Mode of Operation

Referring to FIG. 1, input window 15 to the calorimeter is a lens which focuses laser beam 12 onto sample 11, with the radiation passing into and out of the temperature controlled enclosure 16 through small holes 17. The calorimeter output is derived from the incremental change in the temperature of sample 11 which corresponds to an irradiation by laser beam 12 having known power and duration. This incremental response is heating-rate-independent to a very high order.

Absolute electrical calibration is obtained by dissipating a known quantity of heat in resistor 23 attached to clamp ring 13. The transient response of the system to such a heat input is different than if the heat were deposited in sample 11 by laser irradiation. However, since to a high degree of accuracy both processes are adiabatic due to the presence of the electronic control device 28, the final equilibrium temperature increment is independent of the means, rate, or location of heat input. Absolute electrical calibration makes it unnecessary to know the sample mass, specific heat, or thermal diffusivity.

Because the equilibrium temperature response is rate independent, sample 11 need not have a fixed geometry; and in fact, sample 11 can be scanned point by point from one side to the other by beam 12. Thus, information on the spatial uniformity of the sample absorptance is provided with a resolution limited only by the diameter of beam 12.

Prior to a measurement being made, the temperature of enclosure 16 is maintained at a predetermined temperature level. That is, enclosure 16 may be kept at either the same temperature as sample 11, or the enclosure temperature may be varied higher or lower than the ambient temperature in turn raising or lowering the sample temperature. An equal initial temperature for sample 11 and enclosure 16 is required to prevent heat exchange. A true adiabatic environment is thus sustained. Temperature equality is accomplished by having the temperature rise of sample 11 sensed by sample temperature sensor 21 and amplified by bridge and voltmeter 22. This change in temperature is indicated to electronic control device 28 via an electrical connector 29. Electronic control device 28 causes the temperature of temperature controlled enclosure 16 to rise precisely in step with the rising temperature of sample 11.

If it is desired to make absorptance measurements at either a higher or lower sample temperature than the ambient temperature, then the enclosure temperature is varied; thereby raising or lowering the sample temperature. The absorptance measurement is begun when the sample temperature and enclosure temperature are equal as discussed above. If low temperature measurements are desired than an enclosure cooler would replace enclosure heater 27.

Referring to FIG. 2, the spatial scan is accomplished by moving base 30 with respect to the beam. Base 30 is propelled by roller chains 34 and adjusting rod 35. This same motion permits sample 11 and enclosure base 30 to be withdrawn completely from the beam. Referring to FIG. 1, with sample 11 and enclosure 16 removed from beam 12, a direct measure of the power of beam 12 is possible using power detector 19 and meter 20 at output window 18 of the instrument.

Figure 4:
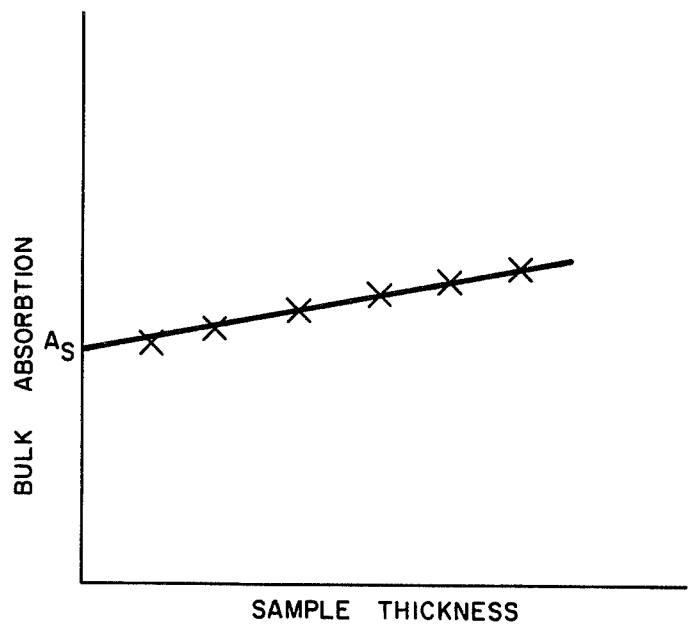
FIG. 4 is a graph of bulk absorption versus thickness and is derived by scanning the sample.

Spatial scanning capability is important in determining the components of the absorption of a thin film or of bulk material. That is, absorption comprises surface absorption and thickness absorption. Surface absorption is constant for a given material while thickness absorption depends on the thickness of the sample. The relationship of bulk absorption to thickness is linear, and a graph of bulk absorption against sample thickness is shown in FIG. 4. If the curve is extrapolated to the absorption axis, then the value of surface absorption is the absorption axis intercept.

The present invention allows a precise and reliable determination of the surface absorption. That is, a wedge-shaped sample may be used to obain the values for the graph of FIG. 4. Previously, it was required to use a number of samples of different thicknesses to obtain the plot. Different samples may vary in uniformity of composition; and, thus, the thickness absorption may be affected. In addition, different samples may be polished differently; and, thus, the surface absorption could vary from sample to sample for the same material. Because the present invention allows the use of one sample of varying thickness, these problems are eliminated. The scanning feature of the present invention is also useful for the investigation of coated and uncoated samples. One section of the sample may be left uncoated with the remainder of the sample being coated. Measurements may then be taken for the coated and uncoated sections which allows a rapid and precise determination of coating film variations. The bulk absorption (A) is computed in the following way:

The specific heat of a material (C) is defined as $$C = \Delta Q / M \Delta T,$$

where M is the mass of the sample; $\Delta Q$ is the energy deposited in the sample; and $\Delta T$ is the incremental temperature response of the sample to the $\Delta Q$ energy. If the same sample is used for two measurements, then the specific heat and mass are the same for both measurements and the equation becomes:

$$\Delta T_{laser} / \Delta T_{cal} \times \Delta Q_{cal} = \Delta Q_{laser},$$

where $\Delta T_{laser}$ is the incremental temperature response to laser irradiation; $\Delta T_{cal}$ is the incremental temperature response to the calibration means; $\Delta Q_{cal}$ is the energy deposited during calibration; and $\Delta Q_{laser}$ is the energy deposited during laser irradiation.

If the laser power is $P_{laser}$, averaged over the irradiation time, $\Delta T_{laser}$, the bulk absorptance A is:

$$A = \Delta Q_{laser}/(P_{laser} \times \Delta T_{laser}).$$

The absorptance can thus be determined without knowing the mass or the specific heat of the sample.

One possible source of error in the invention is the stray light which is absorbed on the clamp ring giving a false signal. The stray light problem is present in calorimeters of all types and is particularly troublesome in vacuum calorimeters because of the additional sources of scattered and reflected light coming from the entrance and exit windows which are necessarily present. Carefully designed and aligned baffles can solve these problems, and the performance of the system can be directly verified by illuminating a sample which has a hole through which the beam passes.

The other major source of stray light is light scattered from the surface or bulk of the sample itself. For many samples most of the scattered light comes from the surfaces, and it is possible to absorb much of this light directly in conical receivers attached to the temperature controlled enclosure. However, bulk scatter is potentially more of a problem, with light scattered directly to the clamp ring. Solutions to this problem include making the ring from material of low absorption and limiting the area of the ring which looks into the sample. Sample scatter becomes much more serious as the wavelength of the beam is reduced. The present invention is capable of absorptance measurements at wavelengths into the near ultraviolet. The calorimeter has a $1 \times 10^{-5}$ absorptance sensitivity for 1 watt laser power.

Although the invention has been illustrated in terms of a preferred embodiment thereof, the invention is not limited to that embodiment. The preferred embodiment employs a laser as the source of energy. However, the invention may be practiced with any suitable energy source. For example, it may be desired to determine the absorptance or ordinary plate glass in response to sunlight irradiation. Other energy sources including narrow beam flood lights or high intensity projectors may also be used without departing from the inventive concept.

What is claimed is:

1. A vacuum, adiabatic, calorimeter, comprising:
    sustaining means for maintaining an adiabatic environment in said calorimeter;
    support means, connected to said sustaining means, for holding a material to be tested in the path of incident electromagnetic energy;
    calibration means, connected to said support means, for supplying a known quantity of energy to said material;
    temperature sensing means, connected to said support means, for calculating temperature changes in said material; and
    scanning means, connected to said sustaining means, for allowing said material to be moved with respect to said electromagnetic energy.

2. A calorimeter according to claim 1 wherein said scanning means includes:
    at least one track having said sustaining means slidably mounted thereon;
    propelling means, connected to said sustaining means, for moving said sustaining means on said track.

3. A calorimeter according to claim 2 wherein said propelling means includes:
    a roller chain; and
    an adjusting rod, connected to said roller chain.

4. A calorimeter according to claim 1 wherein said sustaining means includes:
    an enclosure; and
    temperature controller means, connected to said enclosure, for keeping said enclosure at a predetermined temperature.

5. A calorimeter according to claim 4 wherein said temperature controller means includes:
    an enclosure temperature sensor connected to said enclosure;
    an enclosure heater connected to said enclosure; and
    an electronic control device connected to said sensor and to said heater.

6. A calorimeter according to claim 1 wherein said temperature sensing means includes a thermistor.

7. A calorimeter according to claim 1 wherein said calibration means includes:
    a precision resistor; and
    a calibration current source connected to said resistor.

8. A vacuum, adiabatic, calorimeter comprising:
    an enclosure for maintaining an adiabatic environment in said calorimeter;
    support means, connected to said enclosure for holding a material to be tested in the path of incident electromagnetic energy;
    calibration means, connected to said support means, for supplying a known quantity of energy to said material;
    temperature sensing means, connected to said support means, for calculating temperature changes in said material;
    temperatured controller means, connected to said enclosure, for keeping said enclosure at a predetermined temperature level; and
    scanning means, connected to said enclosure, for allowing said enclosure to be moved with respect to said electromagnetic energy.

9. A calorimeter according to claim 8 wherein said scanning means includes:
    at least one track having said enclosure mounted thereon; and
    propelling means, connected to said enclosure, for moving said enclosure along said track.

10. A calorimeter according to claim 9 wherein said propelling means includes:
    a roller chain; and
    an adjusting rod, connected to said roller chain.

* * * * *